(12) United States Patent
Weisenburgh, II et al.

(10) Patent No.: US 8,465,422 B2
(45) Date of Patent: Jun. 18, 2013

(54) RETRACTOR WITH INTEGRATED WOUND CLOSURE

(75) Inventors: William B. Weisenburgh, II, Maineville, OH (US); Jerome R. Morgan, Cincinnati, OH (US); Christopher J. Hess, Cincinnati, OH (US); Carl J. Shurtleff, Mason, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 747 days.

(21) Appl. No.: 12/479,030

(22) Filed: Jun. 5, 2009

(65) Prior Publication Data

US 2010/0312064 A1    Dec. 9, 2010

(51) Int. Cl.
  *A61B 1/32* (2006.01)
(52) U.S. Cl.
  USPC .......................................... 600/217; 600/206
(58) Field of Classification Search
  USPC ................ 606/150, 215–217, 232–233, 144, 606/228, 139, 148; 600/114, 201–210
  See application file for complete search history.

(56) References Cited

U.S. PATENT DOCUMENTS

| | | |
|---|---|---|
| 2,129,391 A | 9/1938 | Wappler |
| 3,402,710 A | 9/1968 | Paleschuck |
| 3,654,965 A | 4/1972 | Gramain |
| 4,112,932 A | 9/1978 | Chiulli |
| 4,306,545 A | 12/1981 | Ivan et al. |
| 4,379,458 A | 4/1983 | Bauer et al. |
| 4,402,683 A | 9/1983 | Kopman |
| 4,417,888 A | 11/1983 | Cosentino et al. |
| 5,010,925 A | 4/1991 | Atkinson et al. |
| 5,091,435 A | 2/1992 | Suzuki et al. |
| 5,183,471 A | 2/1993 | Wilk |
| 5,197,955 A | 3/1993 | Stephens et al. |

(Continued)

FOREIGN PATENT DOCUMENTS

| | | |
|---|---|---|
| DE | 19814576 A1 | 10/1999 |
| DE | 20022005 U1 | 4/2001 |

(Continued)

OTHER PUBLICATIONS

U.S. Appl. No. 12/420,202 ("Surgical Access Device Having Removable and Replaceable Components" of Shelton et al.).

(Continued)

*Primary Examiner* — Heidi M Eide
(74) *Attorney, Agent, or Firm* — Nutter McClennen & Fish LLP

(57) ABSTRACT

Methods and devices are provided to allow the same component used to access a surgical site to assist in closing the surgical opening in which it was disposed. In one exemplary embodiment a flexible retractor is provided that includes proximal and distal ends and a lumen extending therethrough. A wound closure component is associated with the flexible retractor and is configured to engage tissue adjacent to a surgical incision in which the retractor is disposed and move tissue from one side of the surgical incision toward a second side of the surgical incision to assist in closing the surgical incision. In one embodiment the wound closure component includes strands of suture having hooks disposed on a distal end. In another embodiment the wound closure component includes a ring having hooks disposed around a circumference of the ring. Exemplary methods for closing a surgical opening are also provided.

11 Claims, 11 Drawing Sheets

U.S. PATENT DOCUMENTS

| | | |
|---|---|---|
| 5,207,213 A | 5/1993 | Auhll et al. |
| 5,209,737 A | 5/1993 | Ritchart et al. |
| 5,209,741 A | 5/1993 | Spaeth |
| 5,235,966 A | 8/1993 | Jamner |
| 5,269,772 A | 12/1993 | Wilk |
| 5,308,336 A | 5/1994 | Hart et al. |
| 5,312,417 A | 5/1994 | Wilk |
| 5,320,611 A | 6/1994 | Bonutti et al. |
| 5,342,315 A | 8/1994 | Rowe et al. |
| 5,366,478 A | 11/1994 | Brinkerhoff et al. |
| 5,385,553 A | 1/1995 | Hart et al. |
| 5,385,560 A | 1/1995 | Wulf |
| 5,391,154 A | 2/1995 | Young |
| 5,431,676 A | 7/1995 | Dubrul et al. |
| 5,443,452 A | 8/1995 | Hart et al. |
| 5,443,484 A | 8/1995 | Kirsch et al. |
| 5,476,475 A | 12/1995 | Gadberry |
| 5,480,410 A | 1/1996 | Cuschieri et al. |
| 5,531,758 A | 7/1996 | Uschold et al. |
| 5,545,179 A | 8/1996 | Williamson, IV |
| 5,562,677 A | 10/1996 | Hildwein et al. |
| 5,569,205 A | 10/1996 | Hart et al. |
| 5,569,254 A | 10/1996 | Carlson et al. |
| 5,584,850 A | 12/1996 | Hart et al. |
| 5,628,732 A | 5/1997 | Antoon, Jr. et al. |
| 5,634,911 A | 6/1997 | Hermann et al. |
| 5,634,937 A | 6/1997 | Mollenauer et al. |
| 5,643,301 A | 7/1997 | Mollenauer |
| 5,653,705 A | 8/1997 | de la Torre et al. |
| 5,653,718 A | 8/1997 | Yoon |
| 5,672,168 A | 9/1997 | de la Torre et al. |
| 5,676,657 A | 10/1997 | Yoon |
| 5,695,448 A | 12/1997 | Kimura et al. |
| 5,707,359 A | 1/1998 | Bufalini |
| 5,752,970 A | 5/1998 | Yoon |
| 5,782,812 A | 7/1998 | Hart et al. |
| 5,797,888 A | 8/1998 | Yoon |
| 5,803,919 A | 9/1998 | Hart et al. |
| 5,814,058 A | 9/1998 | Carlson et al. |
| 5,827,319 A | 10/1998 | Carlson et al. |
| 5,843,040 A | 12/1998 | Exline |
| 5,865,807 A | 2/1999 | Blake, III |
| 5,868,762 A | 2/1999 | Cragg et al. |
| 5,882,344 A | 3/1999 | Stouder, Jr. |
| 5,891,013 A | 4/1999 | Thompson |
| 5,899,208 A | 5/1999 | Bonadio |
| 5,906,577 A | 5/1999 | Beane et al. |
| 5,946,280 A | 8/1999 | Ohkubo |
| 5,957,913 A | 9/1999 | de la Torre et al. |
| 5,964,782 A * | 10/1999 | Lafontaine et al. ............ 606/213 |
| 5,990,382 A | 11/1999 | Fox |
| 5,997,515 A | 12/1999 | de la Torre et al. |
| 6,024,736 A | 2/2000 | de la Torre et al. |
| RE36,702 E | 5/2000 | Green et al. |
| 6,056,766 A | 5/2000 | Thompson et al. |
| 6,066,090 A | 5/2000 | Yoon |
| 6,077,288 A | 6/2000 | Shimomura et al. |
| 6,080,174 A | 6/2000 | Dubrul et al. |
| 6,086,603 A | 7/2000 | Termin et al. |
| 6,120,513 A | 9/2000 | Bailey et al. |
| 6,123,689 A | 9/2000 | To et al. |
| 6,142,396 A | 11/2000 | Gallus |
| 6,142,936 A | 11/2000 | Beane et al. |
| 6,162,196 A | 12/2000 | Hart et al. |
| 6,217,555 B1 | 4/2001 | Hart et al. |
| 6,245,052 B1 | 6/2001 | Orth et al. |
| 6,258,069 B1 | 7/2001 | Carpentier et al. |
| 6,277,064 B1 | 8/2001 | Yoon |
| 6,315,770 B1 | 11/2001 | de la Torre et al. |
| 6,319,246 B1 | 11/2001 | de la Torre et al. |
| 6,325,812 B1 | 12/2001 | Dubrul et al. |
| 6,348,034 B1 | 2/2002 | Thompson |
| 6,352,503 B1 | 3/2002 | Matsui et al. |
| 6,440,061 B1 | 8/2002 | Wenner et al. |
| 6,440,063 B1 | 8/2002 | Beane et al. |
| 6,447,489 B1 | 9/2002 | Peterson |
| 6,454,783 B1 | 9/2002 | Piskun |
| 6,458,077 B1 | 10/2002 | Boebel et al. |
| 6,488,620 B1 | 12/2002 | Segermark et al. |
| 6,551,270 B1 | 4/2003 | Bimbo et al. |
| 6,551,282 B1 | 4/2003 | Exline et al. |
| 6,589,167 B1 | 7/2003 | Shimomura et al. |
| 6,605,063 B2 | 8/2003 | Bousquet |
| 6,669,674 B1 | 12/2003 | Macoviak et al. |
| 6,702,787 B2 | 3/2004 | Racenet et al. |
| 6,706,033 B1 | 3/2004 | Martinez et al. |
| 6,706,050 B1 | 3/2004 | Giannadakis |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,972,026 B1 | 12/2005 | Caldwell et al. |
| 7,014,628 B2 | 3/2006 | Bousquet |
| 7,052,454 B2 | 5/2006 | Taylor |
| 7,083,626 B2 | 8/2006 | Hart et al. |
| 7,118,528 B1 | 10/2006 | Piskun |
| 7,163,510 B2 | 1/2007 | Kahle et al. |
| 7,163,525 B2 | 1/2007 | Franer |
| 7,214,185 B1 | 5/2007 | Rosney et al. |
| 7,229,408 B2 | 6/2007 | Douglas et al. |
| 7,338,473 B2 | 3/2008 | Campbell et al. |
| 7,344,547 B2 | 3/2008 | Piskun |
| 7,371,227 B2 | 5/2008 | Zeiner |
| 7,393,322 B2 | 7/2008 | Wenchell |
| 7,449,011 B2 | 11/2008 | Wenchell et al. |
| 7,481,795 B2 | 1/2009 | Thompson et al. |
| 2002/0156432 A1 | 10/2002 | Racenet et al. |
| 2003/0028179 A1 | 2/2003 | Piskun |
| 2003/0139756 A1 | 7/2003 | Brustad |
| 2003/0216770 A1 | 11/2003 | Persidsky et al. |
| 2004/0015185 A1 | 1/2004 | Ewers et al. |
| 2004/0019322 A1 | 1/2004 | Hoffmann |
| 2004/0082969 A1 | 4/2004 | Kerr |
| 2004/0092965 A1* | 5/2004 | Parihar .................... 606/144 |
| 2004/0106942 A1 | 6/2004 | Taylor et al. |
| 2004/0117032 A1 | 6/2004 | Roth |
| 2004/0138528 A1 | 7/2004 | Richter et al. |
| 2004/0199121 A1 | 10/2004 | Wenchell et al. |
| 2004/0215063 A1 | 10/2004 | Bonadio et al. |
| 2004/0230160 A1 | 11/2004 | Blanco |
| 2004/0230161 A1 | 11/2004 | Zeiner |
| 2004/0254426 A1 | 12/2004 | Wenchell |
| 2005/0020884 A1 | 1/2005 | Hart et al. |
| 2005/0033342 A1 | 2/2005 | Hart et al. |
| 2005/0085842 A1 | 4/2005 | Eversull et al. |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0192483 A1 | 9/2005 | Bonadio et al. |
| 2005/0209608 A1 | 9/2005 | O'Heeron |
| 2005/0215862 A1 | 9/2005 | Larson et al. |
| 2005/0216028 A1 | 9/2005 | Hart et al. |
| 2005/0222582 A1 | 10/2005 | Wenchell |
| 2005/0267419 A1 | 12/2005 | Smith |
| 2005/0273132 A1 | 12/2005 | Shluzas et al. |
| 2005/0277946 A1 | 12/2005 | Greenhalgh |
| 2006/0012965 A1 | 1/2006 | Beall et al. |
| 2006/0019592 A1 | 1/2006 | Kupferberg et al. |
| 2006/0019723 A1 | 1/2006 | Vorenkamp et al. |
| 2006/0020241 A1 | 1/2006 | Piskun et al. |
| 2006/0020281 A1 | 1/2006 | Smith |
| 2006/0021061 A1 | 1/2006 | Cerri et al. |
| 2006/0021891 A1 | 2/2006 | Franer et al. |
| 2006/0025813 A1 | 2/2006 | Shelton et al. |
| 2006/0030755 A1 | 2/2006 | Ewers et al. |
| 2006/0071432 A1 | 4/2006 | Staudner |
| 2006/0129165 A1 | 6/2006 | Edoga et al. |
| 2006/0212061 A1 | 9/2006 | Wenchell |
| 2006/0212062 A1 | 9/2006 | Farascioni |
| 2006/0217665 A1 | 9/2006 | Prosek |
| 2006/0224129 A1 | 10/2006 | Beasley et al. |
| 2006/0224164 A1 | 10/2006 | Hart et al. |
| 2006/0229501 A1 | 10/2006 | Jensen et al. |
| 2006/0241651 A1 | 10/2006 | Wilk |
| 2006/0241671 A1 | 10/2006 | Greenhalgh |
| 2006/0247498 A1 | 11/2006 | Bonadio et al. |
| 2006/0247500 A1 | 11/2006 | Voegele et al. |
| 2006/0247516 A1 | 11/2006 | Hess et al. |

| | | | | | | |
|---|---|---|---|---|---|---|
| 2006/0247586 A1 | 11/2006 | Voegele et al. | EP | 1219251 A1 | 7/2002 | |
| 2006/0247673 A1 | 11/2006 | Voegele et al. | EP | 1219252 A1 | 7/2002 | |
| 2006/0247678 A1 | 11/2006 | Weisenburgh et al. | EP | 1219253 A1 | 7/2002 | |
| 2006/0258899 A1 | 11/2006 | Gill et al. | EP | 1350476 | 10/2003 | |
| 2006/0264706 A1 | 11/2006 | Piskun | EP | 1702575 A2 | 9/2006 | |
| 2006/0270911 A1 | 11/2006 | Voegele et al. | EP | 1731105 A1 | 12/2006 | |
| 2007/0049966 A1 | 3/2007 | Bonadio et al. | EP | 1774918 A1 | 4/2007 | |
| 2007/0060939 A1 | 3/2007 | Lancial et al. | EP | 2119404 A1 | 11/2009 | |
| 2007/0085232 A1 | 4/2007 | Brustad et al. | FR | 2710270 A1 | 3/1995 | |
| 2007/0088202 A1 | 4/2007 | Albrecht et al. | JP | 2006320750 | 11/2006 | |
| 2007/0088204 A1 | 4/2007 | Albrecht et al. | WO | 9407552 A1 | 4/1994 | |
| 2007/0088258 A1 | 4/2007 | Wenchell et al. | WO | 9602297 A1 | 2/1996 | |
| 2007/0088277 A1 | 4/2007 | McGinley et al. | WO | 9608897 A1 | 3/1996 | |
| 2007/0118021 A1 | 5/2007 | Pokorney | WO | 9636283 A1 | 11/1996 | |
| 2007/0118175 A1 | 5/2007 | Butler et al. | WO | 9743958 A1 | 11/1997 | |
| 2007/0151566 A1 | 7/2007 | Kahle et al. | WO | 0032263 A1 | 6/2000 | |
| 2007/0185453 A1 | 8/2007 | Michael et al. | WO | 0041759 A1 | 7/2000 | |
| 2007/0208312 A1 | 9/2007 | Norton et al. | WO | 0108563 A2 | 2/2001 | |
| 2007/0255219 A1 | 11/2007 | Vaugh et al. | WO | 0217800 A2 | 3/2002 | |
| 2008/0009797 A1 | 1/2008 | Stellon et al. | WO | 2004030515 A2 | 4/2004 | |
| 2008/0025519 A1 | 1/2008 | Yu et al. | WO | 2005000454 A1 | 1/2005 | |
| 2008/0027476 A1 | 1/2008 | Piskun | WO | 2005002454 A1 | 1/2005 | |
| 2008/0051739 A1 | 2/2008 | McFarlane | WO | 2005087112 A1 | 9/2005 | |
| 2008/0058728 A1 | 3/2008 | Soltz et al. | WO | 2005094432 A2 | 10/2005 | |
| 2008/0065021 A1 | 3/2008 | Jenkins et al. | WO | 2005097019 A2 | 10/2005 | |
| 2008/0086080 A1 | 4/2008 | Mastri et al. | WO | 2005097234 A2 | 10/2005 | |
| 2008/0119821 A1 | 5/2008 | Agnihotri et al. | WO | 2006057982 A2 | 6/2006 | |
| 2008/0132765 A1 | 6/2008 | Beckman et al. | WO | 2007008741 A1 | 1/2007 | |
| 2008/0255519 A1 | 10/2008 | Piskun et al. | WO | 2007119232 A2 | 10/2007 | |
| 2008/0281161 A1 | 11/2008 | Albrecht et al. | WO | 2008024502 A2 | 2/2008 | |
| 2009/0005799 A1 | 1/2009 | Franer et al. | WO | 2008028149 A2 | 3/2008 | |
| 2009/0082731 A1 | 3/2009 | Moreno | WO | 2008121294 A1 | 10/2008 | |
| 2009/0118587 A1 | 5/2009 | Voegele et al. | WO | 2009035663 A2 | 3/2009 | |
| 2009/0187079 A1 | 7/2009 | Albrecht et al. | | | | |
| 2009/0270685 A1 | 10/2009 | Moreno et al. | | | | |
| 2009/0270686 A1 | 10/2009 | Duke et al. | | | | |
| 2009/0270818 A1 | 10/2009 | Duke | | | | |
| 2010/0010310 A1 | 1/2010 | Weisenburgh, II et al. | | | | |
| 2010/0081863 A1 | 4/2010 | Hess et al. | | | | |
| 2010/0081864 A1 | 4/2010 | Hess et al. | | | | |
| 2010/0081871 A1 | 4/2010 | Widenhouse et al. | | | | |
| 2010/0081880 A1 | 4/2010 | Widenhouse et al. | | | | |
| 2010/0081881 A1 | 4/2010 | Murray et al. | | | | |
| 2010/0081882 A1 | 4/2010 | Hess et al. | | | | |
| 2010/0081883 A1 | 4/2010 | Murray et al. | | | | |
| 2010/0081995 A1 | 4/2010 | Widenhouse et al. | | | | |
| 2010/0228090 A1 | 9/2010 | Weisenburgh, II et al. | | | | |
| 2010/0228091 A1 | 9/2010 | Widenhouse et al. | | | | |
| 2010/0228092 A1 | 9/2010 | Ortiz et al. | | | | |
| 2010/0228094 A1 | 9/2010 | Ortiz et al. | | | | |
| 2010/0228096 A1 | 9/2010 | Weisenburgh, II et al. | | | | |
| 2010/0228198 A1 | 9/2010 | Widenhouse et al. | | | | |
| 2010/0249525 A1 | 9/2010 | Shelton, IV et al. | | | | |
| 2010/0261970 A1 | 10/2010 | Shelton, IV et al. | | | | |
| 2010/0261972 A1 | 10/2010 | Widenhouse et al. | | | | |
| 2010/0261974 A1 | 10/2010 | Shelton, IV et al. | | | | |
| 2010/0262080 A1 | 10/2010 | Shelton, IV et al. | | | | |
| 2010/0268162 A1 | 10/2010 | Shelton, IV et al. | | | | |
| 2010/0274093 A1 | 10/2010 | Shelton, IV | | | | |
| 2010/0280327 A1 | 11/2010 | Nobis et al. | | | | |
| 2010/0312060 A1 | 12/2010 | Widenhouse et al. | | | | |
| 2010/0312061 A1 | 12/2010 | Hess et al. | | | | |
| 2010/0312062 A1 | 12/2010 | Cropper et al. | | | | |
| 2010/0312063 A1 | 12/2010 | Hess et al. | | | | |
| 2010/0312064 A1 | 12/2010 | Weisenburgh, II et al. | | | | |
| 2010/0312065 A1 | 12/2010 | Shelton, IV et al. | | | | |
| 2010/0312066 A1 | 12/2010 | Cropper et al. | | | | |
| 2010/0312189 A1 | 12/2010 | Shelton, IV et al. | | | | |

FOREIGN PATENT DOCUMENTS

| | | | |
|---|---|---|---|
| EP | 568383 A1 | 11/1993 | |
| EP | 577400 A1 | 1/1994 | |
| EP | 0637431 A1 | 2/1995 | |
| EP | 646358 A1 | 4/1995 | |
| EP | 709918 | 5/1996 | |
| EP | 0776231 B1 | 6/1997 | |
| EP | 950376 | 10/1999 | |

OTHER PUBLICATIONS

International Search Report and Written Opinion for International App. No. PCT/US2010/036811 dated Sep. 14, 2010 (6 pages).

International Search Report, from PCT/US10/36829, mailed Sep. 9, 2010 (5 pages).

European Search Report, EP 10250732, dated Jul. 28, 2010.

International Search Report and Written Opinion for Application No. PCT/US2010/037190, dated Sep. 22, 2010 (15 pages).

"Surgeon performs single-port laparoscopic surgery > Kidney removal with instructions inserted through single port access SPA > One Port Umbilicus Surgery OPUS > Uretero-pelvic junction repair > Bilateral pyeloplasty > Triport > Quadport > R-Port laparoscopic access device > Advanced Surgical Concepts ASC" Ideas for Surgery.com, Dec. 2007, 4 pages.

Desai, Mihir M. et al., "Laparoscopic and Robtic Urology-Scarless single port transumbilical nephrectomy and pyeloplasty: first clinical report," Journal Compilation, 2008 BJU International, 101, pp. 83-88.

Lee D, et al. Novel Approach to Minimizing Trocar Sites during Challenging Hand-Assisted Laparoscopic Surgery Utilizing the GelPort: Trans-Gel Instrument and Utilization, Journal of Endourology, vol. 17, No. 2, Mar. 2003, pp. 69-71.

Nakajima K, et al. Hand-assisted laparoscopic colorectal surgery using GelPort, Surg Endosc. Jan. 2004; 18(1)102-5. Epub Sep. 10, 2003.

Nakajima K, et al. Use of the surgical towel in colorectal hand-assisted laparoscopic surgery (HALS), Surg Endosc. Mar. 2004; 18(3):552-3.

Patel, R. et al. "Hand-Assisted Laparoscopic Devices: The Second Generation," Journal of Endourology, vol. 18, No. 7, Sep. 2004, pp. 649-653.

Rane, A. et al., "Single-Port Access Nephrectomy and Other Laparoscopic Urologic Procedures Using a Novel Laparoscopic Port (R-Port)," Urology, Aug. 2008; 72(2):260-264.

International Search Report and Written Opinion for Application No. PCT/US2010/036806, dated Sep. 3, 2010 (8 pages).

International Search Report and Written Opinion for Application No. PCT/US2010/036820, dated Oct. 22, 2010 (18 pages).

* cited by examiner

FIG. 1
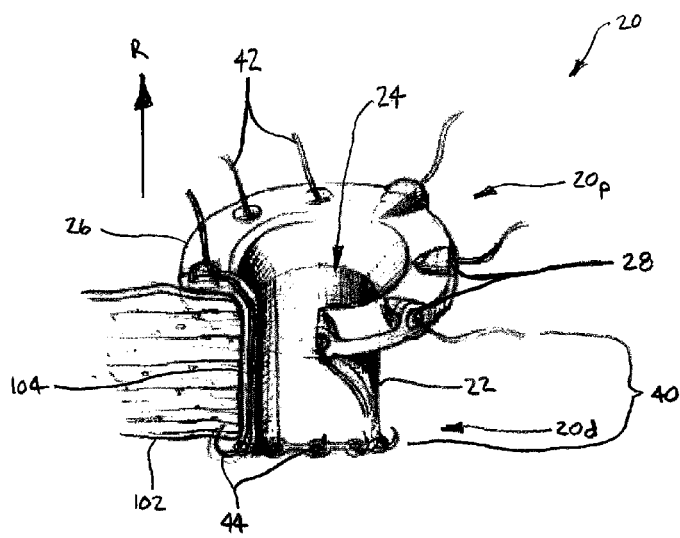
FIG. 2A  FIG. 2B  FIG. 2C  FIG. 2D
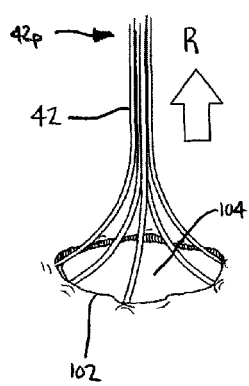 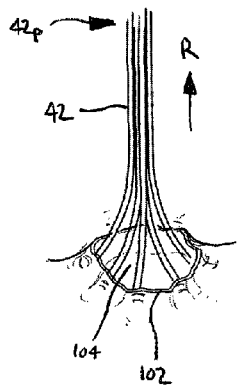 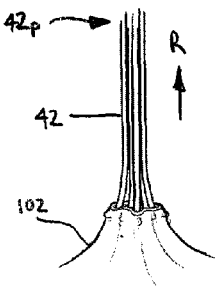 

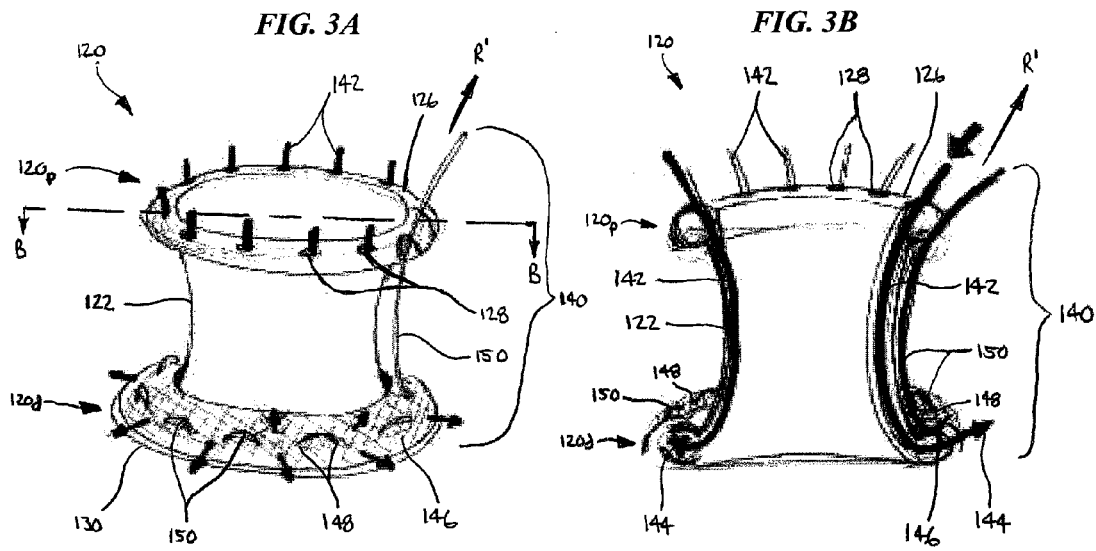
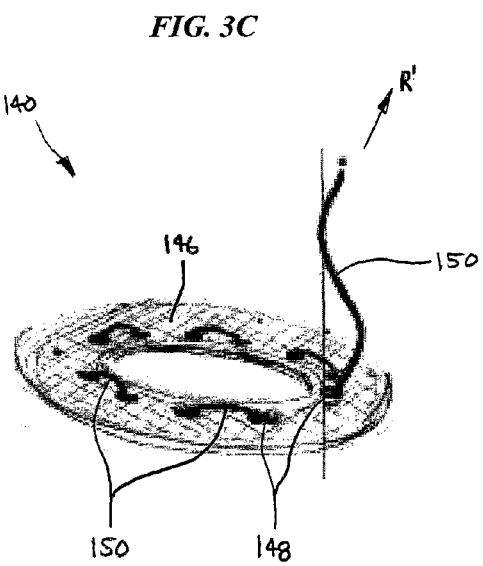

RETRACTOR WITH INTEGRATED WOUND CLOSURE

FIELD

The present invention relates to methods and devices that can both retract tissue away from a surgical incision and assist in closing the surgical incision.

BACKGROUND

Minimally invasive surgical techniques such as endoscopies and laparoscopies are often preferred over traditional open surgeries because the recovery time, pain, and surgery-related complications are typically less with minimally invasive surgical techniques. In many laparoscopic procedures, the abdominal cavity is insufflated with carbon dioxide gas to a pressure of approximately 15 mm Hg. The abdominal wall is pierced and a cannula or trocar that is approximately 5 to 10 mm in diameter is inserted into the abdominal cavity. Surgeons can then perform a variety of diagnostic procedures, such as visual inspection or removal of a tissue sample for biopsy, or treatment procedures, such as removal of a polyp or tumor or restructuring tissue.

Because of the rise in popularity of minimally invasive surgeries, there has been significant development with respect to the procedures and the instruments used in such procedures. For example, in some procedures a single incision at the navel can be sufficient to provide access to a surgical site. This is because the umbilicus can be a preferred way to access an abdominal cavity in a laparoscopic procedure. The umbilical incision can be easily enlarged without significantly compromising cosmesis and without significantly increasing the chances of wound complications, thus allowing multiple instruments to be introduced through a single incision.

In one common form of a single site laparoscopy procedure, an incision having a diameter of approximately 20 to 35 millimeters is formed and a surgical access device is disposed therein. The surgical access device forms a seal with the tissue of the opening and also forms a seal between the surgical site and the outside environment. The device typically includes a flexible retractor with one or more seal elements disposed in the retractor. Instruments can then be inserted into the seal elements for use at the surgical site while the seal between the surgical site and the outside environment is maintained. While having a surgical incision with a diameter of approximately 20 to 35 millimeters can improve the range of motion and access for instruments disposed in the surgical access device, and can also be quite useful for removing various specimen from the surgical site, it can sometimes require a significant amount of effort to close the surgical incision once the procedure is complete.

Accordingly, it would be desirable for a surgical access device, or a component of a surgical access device, such as a retractor, to include one or more features that help make closing the surgical incision in which the device was disposed easier.

SUMMARY

Methods and devices are generally provided that allow for a surgical site to be accessed through a component of a surgical access device that is disposed in a surgical opening during a surgical procedure, and further, allow the component of the surgical access device to assist in closing the surgical opening in which the component was disposed. In one embodiment a surgical access device includes a housing having an opening extending therethrough and which is configured to be positioned adjacent to a surgical incision, a flexible retractor that can be removably and replaceably coupled to the housing and which is configured to be positioned within the surgical incision to provide access to a body cavity, and a wound closure component associated with a distal end of the retractor. The wound closure component can be configured to engage tissue adjacent to the surgical incision and can selectively move tissue from one side of the surgical incision toward a second side of the surgical incision. Such movement can assist in closing the surgical incision.

In one embodiment the wound closure component can include hooks. Each of the hooks can be coupled to a strand of suture that is removably disposed in at least a portion of the retractor. The hooks can be configured to engage the tissue that is adjacent to the surgical incision. A proximal end of each strand of suture can be configured to be approximated and pulled together in a direction away from the surgical incision. This, in turn, can pull closer together the tissue that is engaged by the hooks. Optionally, an actuation mechanism can be coupled to the proximal ends of the strands of suture. The actuation mechanism can be configured to approximate the strands of suture toward each other in a direction away from the surgical incision.

In another embodiment the wound closure component can include a ring having hooks disposed around a circumference of the ring. The hooks can be configured to engage the tissue that is adjacent to the surgical incision. The hooks can further be configured to be deployed into the tissue in response to a designated movement of the retractor. For example, the hooks can be deployed upon rotation of the retractor. In one embodiment the hooks can be configured to be approximated toward each other in response to a force that is applied to the retractor in a direction away from the surgical incision. The ring can include a hinge that is located along the circumference of the ring. In one embodiment the ring can be configured to be removed from the tissue in which it is disposed after the plurality of hooks are approximated toward each other.

An exemplary embodiment of a flexible retractor for use in a surgical procedure can include proximal and distal ends with a lumen extending therethrough to define a working channel and a wound closure component associated with the distal end of the retractor. The wound closure component can be configured to engage tissue adjacent to a surgical incision and approximate tissue adjacent to the surgical incision to assist in closing the surgical incision. In one embodiment the wound closure component can include hooks. Each of the hooks can be coupled to a strand of suture, and further, can be configured to engage the tissue adjacent to the surgical incision. Additionally, the strands of suture can be configured to be manipulated in such a way that the tissue engaged by the hooks is approximated. In another embodiment the wound closure component can include a ring having hooks disposed around its circumference. The hooks can be configured to engage the tissue adjacent to the surgical incision. In one embodiment the hooks can be configured to engage tissue in response to a designated movement of the retractor. For example, rotation of the retractor can cause the hooks to engage the tissue adjacent to the surgical incision. Further, the ring can include a hinge disposed thereon. In such an embodiment, the ring can be configured, for example, such that when the ring is moved in a direction away from the surgical incision, the ring pulls tissue adjacent to the surgical incision toward other tissue adjacent to the surgical incision.

One exemplary embodiment of a method for repairing a surgical wound includes positioning a surgical access retractor through an opening in tissue. The retractor can include a wound closure component. The wound closure component can engage tissue adjacent to a distal end of the retractor. The wound closure component can also be manipulated to approximate tissue adjacent to the opening in tissue, which in turn can close the surgical wound. The approximated tissue can then be sutured. In one embodiment, manipulating the wound closure component can include moving the wound closure component toward an outside environment. In another embodiment, manipulating the wound closure component can include cinching strands of suture coupled to the tissue adjacent to the distal end of the retractor toward each other.

BRIEF DESCRIPTION OF DRAWINGS

This invention will be more fully understood from the following detailed description taken in conjunction with the accompanying drawings, in which:

FIG. 1 is a perspective view of one exemplary embodiment of a retractor having a wound closure component disposed therein and having a portion of a sidewall of the retractor removed;

FIG. 2A is a perspective view of suture strands of the wound closure component of FIG. 1 engaged with tissue;

FIG. 2B is a perspective view of the suture strands of FIG. 2A showing the strands being moved to bring the tissue with which they are engaged closer together;

FIG. 2C is a perspective view of the suture strands of FIG. 2B showing the strands being moved further to bring the tissue with which they are engaged in contact;

FIG. 2D is a perspective view of the tissue of FIG. 2C sutured together;

FIG. 3A is another exemplary embodiment of a retractor, the retractor having a wound closure component disposed therein;

FIG. 3B is a cross-sectional side view of the retractor of FIG. 3A taken at line B-B;

FIG. 3C is a perspective view of a distal ring of the wound closure component of FIG. 3A;

DETAILED DESCRIPTION

Figure 4A:
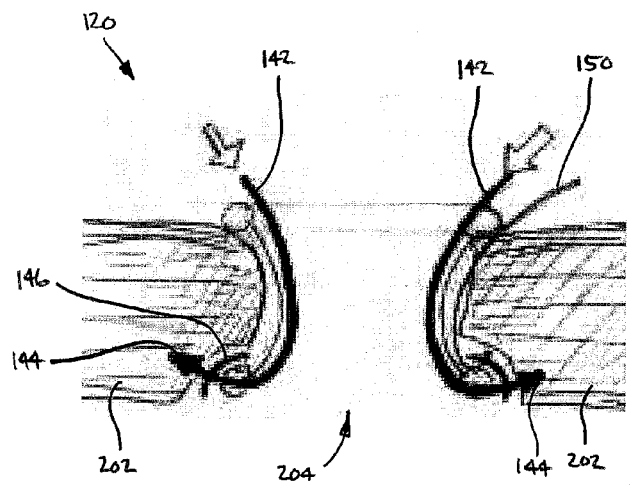
FIG. 4A is a cross-sectional side view of the retractor of FIG. 3A taken at line B-B disposed in a surgical incision having the wound closure component engaged with tissue adjacent to the surgical incision.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Like-numbered components of the embodiments generally have similar features, and thus within a particular embodiment each feature of each like-numbered component is not necessarily fully elaborated upon. A person having skill in the art will recognize that features of one component can generally be incorporated into other like-numbered components.

A surgical access device is generally provided for minimally-invasive surgeries such as laparoscopic surgeries. The surgical access device can be disposed in a body to allow for access to a surgical site from outside of the body. The device can generally be configured to receive one or more instruments through the device so that the instruments can be used to perform a desired procedure. The device can have a number of different components, or it can be a single component. One component that can be used as a surgical access device, or in conjunction with a surgical access device, is a retractor. More specifically, a retractor can be disposed in a surgical incision or opening and can provide access from an outside environment to a surgical site, such as a body cavity. The retractor can form a seal between tissue of the incision in which it is disposed and the retractor itself. Further, the retractor can be associated with or include one or more seal elements disposed therein. The retractor, in conjunction with the seal elements, can form a seal between the surgical location and the outside environment. Procedures can be performed by disposing instruments in the seal elements, and once a procedure is complete, the retractor and seal elements can be removed from the surgical opening and the surgical opening or wound can be closed. The terms "surgical opening," "incision," and "wound" are used interchangeably throughout.

In exemplary embodiments the retractor can include one or more features to assist in closing the surgical incision in which it is disposed. Accordingly, as or after the retractor is removed, one or more wound closure components can be used to help close the wound. The wound closure component(s) can be associated or incorporated with the retractor before, while, or after the retractor is disposed in the surgical incision. In one embodiment, as the retractor is removed, a wound closure component can selectively move tissue from one side of the surgical incision toward a second side of the surgical incision. By associating or incorporating a wound closure component with the retractor, a surgical incision can be closed without inserting additional tools into the body. This consolidation of functions into a single device is a novel approach for accessing a surgical site through an opening and then closing the opening. Wound closure components can have a variety of configurations, some of which are described below, but generally a wound closure component can be configured to assist with closing a surgical incision following a surgical procedure.

A retractor associated with a wound closure component can be configured to operate on its own as a surgical access device, but it can also be incorporated into a surgical access device having other components. A surgical access device can include any number of components and features, but in one exemplary embodiment it can include a housing with an opening extending therethrough and capable of receiving a retractor with a wound closure component associated therewith. The housing can be configured to be located outside of the body and be positioned adjacent to the surgical opening. The retractor can be removably and replaceably coupled to the housing, for instance by way of male and female components associated with the retractor and housing, a snap-fit configuration, an interference-fit configuration, or any number of ways by which two components can be coupled.

The surgical access device can also include one or more seal elements. The seal elements can be generally flexible and can be configured to be disposed, at least in part, in the retractor, or alternatively, the seal elements can be configured to be coupled to the housing, proximal of the retractor. The seal elements can have bodies and can be generally configured to both receive instruments through a sealable opening formed in the bodies for use at a surgical site and to maintain a seal between a surgical site and an outside environment, thereby limiting or preventing fluid from passing therebetween. The sealable opening can be configured to form a seal itself when no instrument is disposed therein, and to conform to and seal around an instrument disposed within the sealable opening. It can be advantageous to have one seal element be configured to receive an instrument for providing insufflation to the surgical site, although in some embodiments the housing and/or retractor can include an opening for providing insufflation.

The seal elements can have a variety of shapes, sizes, and features, depending at least in part on the size of the incision, housing, and/or retractor in which they will be disposed, the surgical device components and instrument with which they will be used, and the type of surgical procedure with which they will be used. Any type of seal element can be used in conjunction with the surgical access devices and/or retractors disclosed herein, including, but not limited to elongate, rounded, gel, multi-layer, duckbill, gimbal, zero-closure, diaphragm, and septum seal elements, each of which can serve particular purposes.

One exemplary embodiment of a retractor 20 having a wound closure component associated therewith is illustrated in FIG. 1. The retractor 20 can include proximal and distal ends 20p, 20d with a lumen 24 extending therethrough to define a working channel. A sidewall or body 22 of the retractor 20 can extend between the proximal and distal ends 20p, 20d to help define the lumen 24. The retractor 20 can be configured to be disposed in a surgical opening 104 formed in tissue 102. Seal elements (not shown) can be at least partially disposed in the lumen 24 to form a seal between a surgical site and an outside environment.

The retractor 20 can be configured to be generally flexible, and thus can be made from a flexible material, such as a polymer. Examples of flexible materials that can be used to form the retractor include polyisoprene, polyurthethane, and silicone. More than one material can be used to form the retractor, and the retractor can include some portions that are more rigid than other portions. For example, more rigid portions of a retractor can be made from materials such as polycarbonate, polyester, polyetherimide, or stainless steel, while more flexible portions can be made from materials such as polyisoprene, polyurthethane, and silicone. Another non-limiting exemplary embodiment of a retractor that can be used with the teachings described herein is described in greater detail in U.S. patent application Ser. No. 12/420,107 entitled "Retractor with Flexible Sleeve" of Shelton et al., and filed on Apr. 8, 2009, which is hereby incorporated by reference in its entirety.

While the retractor can be configured to have a variety of shapes and sizes, depending at least in part on the size of the incision in which it will be disposed, additional components with which it will be used, and the type of surgical procedure with which it will be used, the retractor 20 in the illustrated embodiment has a body that is generally cylindrical and includes a flange 26 at the proximal end 20p. The flange 26 can help retract tissue 102 at a proximal end of the surgical incision 104. In alternative embodiments the retractor can include a flange at the distal end 20d to also assist in retracting tissue away from the surgical opening. The wound closure component 40 of the retractor 20 can also help retract tissue 102 at a distal end of the surgical incision 104.

As shown, the flange 26 at the proximal end 20p of the retractor 20 can have openings 28 formed therein. The openings 28 can extend through the body 22 of the retractor 20 and out the distal end 20d. A portion of the wound closure component 40 can be disposed in the openings 28. In the illustrated embodiment the wound closure component 40 includes suture strands 42 disposed in each opening 28, as well as barbs or hooks 44 that are configured to engage tissue 102 adjacent the surgical incision 104 near the distal end 20d of the retractor 20, which can be attached to distal ends of the strands 42. The length of the suture strands 42, and the size and shape of the hooks 44, can depend on a variety of different factors, including but not limited to the sizes and shapes of the components with which they are associated and the type of surgical procedure with which the strands and hooks are used. Nevertheless, generally the strands 42 are long enough so that they can be operated from a location outside of the body and can engage a distal end of the surgical incision 104 and the hooks 44 are configured to promote engagement with tissue 102 near the distal end of the surgical incision. The hooks 44 can be made of a variety of materials, including, for example, stainless steel or nitinol. The hooks 44 can generally be implantable, and in one embodiment the hooks are bioabsorbable.

In use, the hooks 44 can engage the tissue 102 in a variety of manners, some of which are disclosed further below with respect to FIGS. 4A-4C and 5A-5G, and can help establish a location for the retractor 20 within the surgical incision 104. The hooks 44 can engage the tissue 102 before, during, or after a surgical procedure is performed, depending on the configuration of the retractor 20. Once a surgical procedure has been performed and closure of the surgical incision 104 is desired, the retractor 20 can be removed from the surgical incision by pulling it in a direction R away from the incision. The suture strands 42 can be configured such that they also pull in the direction R away from the surgical opening 104 when the retractor 20 pulls away, or alternatively, they can be configured to remain in place while the retractor is removed.

FIGS. 2A-2D illustrate closure of a surgical incision 104 using retractor 20 of the type shown in FIG. 1. As illustrated in FIG. 2A, following removal of the retractor, a proximal end 42p of the suture strands 42 can be pulled in the direction R away from the surgical opening. As shown, each of the suture strands 42 can be cinched together and pulled at the same time. This eases the closing of the wound, although cinching and pulling each of the suture strands 42 together is only one way in which the wound can be closed. As shown in FIGS. 2B and 2C, further pulling in the direction R can draw the tissue 102 upward in the direction R and can also bring the tissue adjacent to the incision 104 closer together or in contact. When the tissue 102 adjacent to the surgical opening 104 is near or in contact, the tissue can be sutured together, as shown in FIG. 2D. Either the suture strands 42 already disposed in the tissue 102 can be used to suture the tissue, or alternatively or additionally, separate suture can be used to suture the two sides of tissue together.

FIGS. 3A-3C illustrate another embodiment of a retractor 120 having a wound closure component 140 disposed therein. The wound closure component 140 includes suture strands 142, barbs or hooks 144, a distal ring 146, and an actuating suture 150. As shown, the suture strands 142 can be disposed in openings 128 of a proximal flange 126 formed in a proximal end 120p of the retractor 120 and can extend both through a body 122 and a distal flange 130 formed in a distal end 120d of the retractor 120, as well as through the distal ring 146 of the wound closure component 140. The hooks 144 can be attached to distal ends of the suture strands 142 and can be configured to engage tissue adjacent to a surgical incision near the distal end 120d of the retractor 120. The distal ring 146 can be removably coupled to the distal flange 130 of the retractor 120 and can include openings 148 for receiving at least one of the suture strands 142 and the actuating suture 150. The actuating suture 150 can be looped through the openings 148 of the distal ring 146, as shown in FIG. 3C, and can be configured to cause the distal ring to collapse by pulling in a direction R'. While in the illustrated embodiment the distal ring 146 is removably coupled to the retractor 120, in other embodiments the distal ring can be the distal flange of the retractor and the distal flange of the retractor can be removable from the remainder of the retractor. Further, although in the illustrated embodiment the suture strands 142 and the actuating suture 150 are separate components, in other embodiments a single suture can be disposed throughout the entirety of the retractor such that pulling the suture strand in a manner similar to the actuating suture 150 can cause the surgical opening to be closed.

Figure 4B:
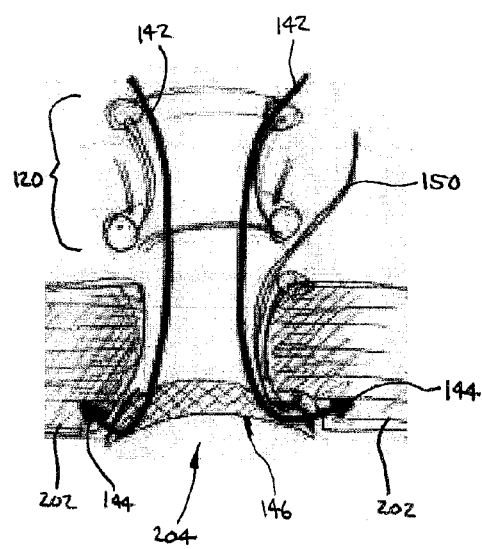
FIG. 4B is a cross-sectional side view of the retractor and wound closure component of FIG. 4A showing the retractor removed from the surgical incision and the wound closure component remaining engaged with the tissue.
Figure 4C:
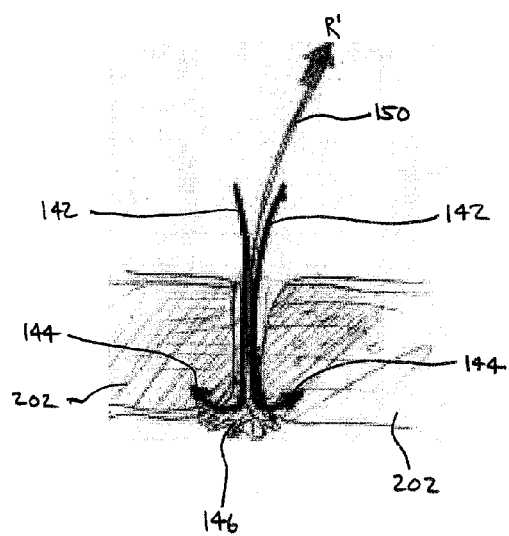
FIG. 4C is a cross-sectional side view of the wound closure component of FIG. 4B showing the wound closure component moving tissue from one side of the surgical incision toward tissue from a second side of the surgical incision.

The operation of the retractor 120 of FIGS. 3A-3C is illustrated in FIGS. 4A-4C. As shown, the retractor 120 can be disposed in a surgical opening 204 formed in tissue 202 and the hooks 144 coupled to the distal end of the suture strands 142 can engage tissue. Upon completion of a surgical procedure, as shown in FIG. 4B, the retractor 120 can be removed from the surgical opening 204 while the wound closure component 140, including suture strands 142, the hooks 144, the distal ring 146, and the actuating suture 150, remain. The retractor 120 can be detached from the distal ring 146 in a number of ways, but in the illustrated embodiment the retractor 120 and the distal ring 146 separate when a separation force X is applied to the retractor that is sufficient to detach the retractor from the ring while the ring remains engaged with the tissue 202 via the hooks 144. The actuating suture 150 can then be pulled in the direction R' away from the surgical opening 204 (FIG. 4C) to cause the distal ring 146 to collapse, which in turn draws the suture strands 142, the hooks 144, and the engaged tissue 202, closer together. The wound 204 can then be sealed by tying off at least one of the suture strands 142 and the actuating suture 150, or using another suture or other mechanism for closing a wound. In alternative embodiments the entire retractor 120 can remain in the surgical opening and can collapse while the wound is being closed.

FIGS. 5A-5G illustrate an embodiment of a surgical access device 210 that includes a wound closure component like those of FIGS. 1-4C and a retractor. More particularly, the surgical access device 210 includes a housing 215, a retractor 220, and a wound closure component 240 that includes suture strands 242 having barbs or hooks 244 coupled to a distal end thereof. As shown, the suture strands 242 are disposed around a circumference of the wound closure component 240. The housing 215 can be positioned adjacent to a surgical incision 304 formed in tissue 302 and can help provide access to a surgical site at a distal end of the incision. While the housing 215 can be configured in such a manner that it can rest against the tissue 302 to form a seal therebetween without needing to be secured by an outside mechanism, sutures or other outside mechanisms can optionally be used to secure the housing to tissue. The housing 215 can also be configured to receive at least one of the retractor 220 and the wound closure component 240. In the illustrated embodiment the housing 215 is coupled to a proximal end 220p of the retractor at a distal end 215d of the housing and is configured to receive the wound closure component 240 at a proximal end 215p of the housing.

The housing 215 can have any number of shapes, sizes, and configurations, depending at least in part on the size of the incision with which it will be used, the surgical device components with which it will be used, and the type of surgical procedure with which it will be used. In the illustrated embodiment the housing 215 is substantially disk-shaped. The housing 215 can be configured to receive one or more seal elements, a retractor, and/or a wound closure component in a removable and replaceable configuration. In some embodiments the seal elements can be disposed in the retractor itself, while in other embodiments the seal elements can be formed in a separate component disposed in the housing, proximal of the retractor. In the illustrated embodiment, as seen in FIG. 5B, seal elements 218 are formed in the wound closure component 240. As also shown in the figures of FIGS. 5A-5G, a proximal end 215p of the housing 215 can be configured to receive the wound closure component 240 and a distal end 215d of the housing can be coupled to a proximal end 220p of the retractor 220, forming a sealed configuration therebetween.

Figure 5A:
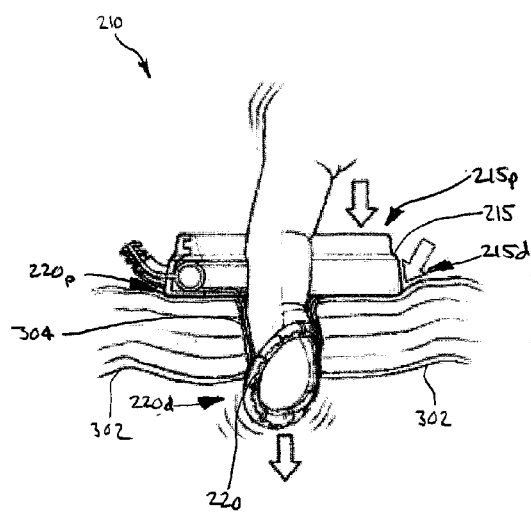
FIG. 5A is a cross-sectional side view of one exemplary embodiment of a surgical access device showing a distal end of a retractor of the device being placed in a surgical incision.
Figure 5B:
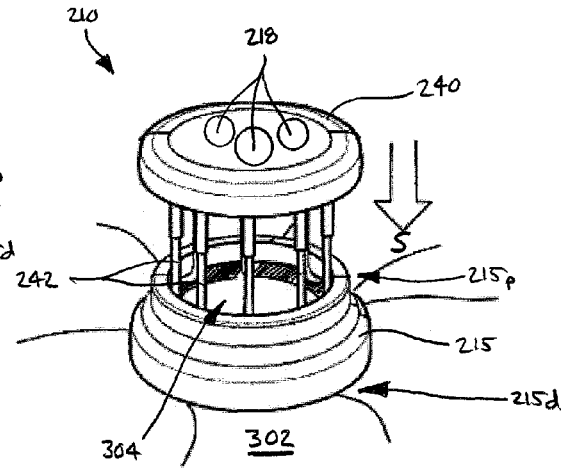
FIG. 5B is a perspective view of the surgical access device of FIG. 5A showing a proximal end of the retractor of the device moving toward a housing of the device and including a wound closure component coupled to the retractor.
Figure 5C:
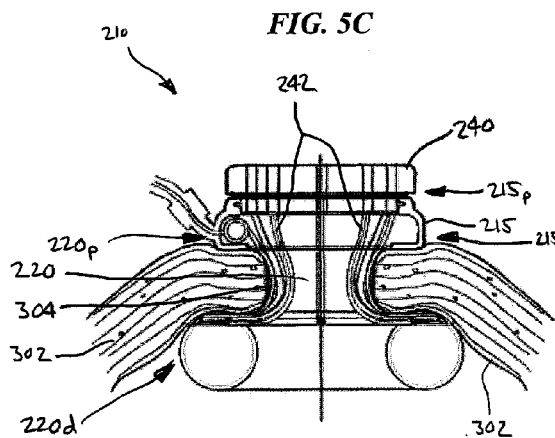
FIG. 5C is a cross-sectional side view of the surgical access device of FIG. 5B showing the proximal end of the retractor engaged with the housing.

In use, as shown in FIG. 5A, a distal end 220d of the retractor 220 can be disposed in a distal end of the surgical incision 304, thereby retracting tissue away from the surgical incision. Subsequently, the wound closure component 240 can be coupled to the proximal end 215p of the housing 215 to form a seal therebetween by moving the wound closure component 240 in a direction S toward the housing 215. The suture strands 242 of the wound closure component 240 can extend through the housing 215 and into the retractor 220, for instance approximately along a sidewall thereof, before terminating near the distal end 220d of the retractor 220.

Figure 5D:
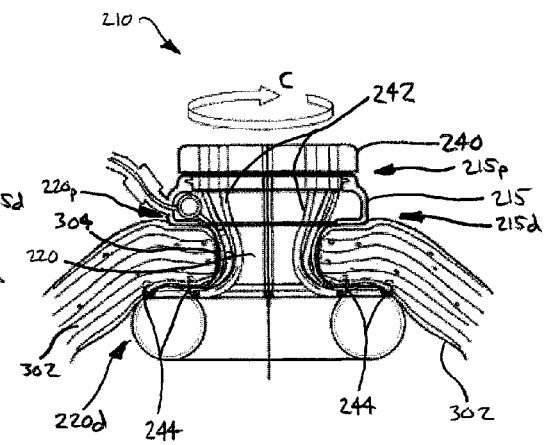
FIG. 5D is a cross-sectional side view of the surgical access device of FIG. 5C showing the retractor being rotated to allow the wound closure component to engage tissue adjacent to the surgical incision.
Figure 5E:
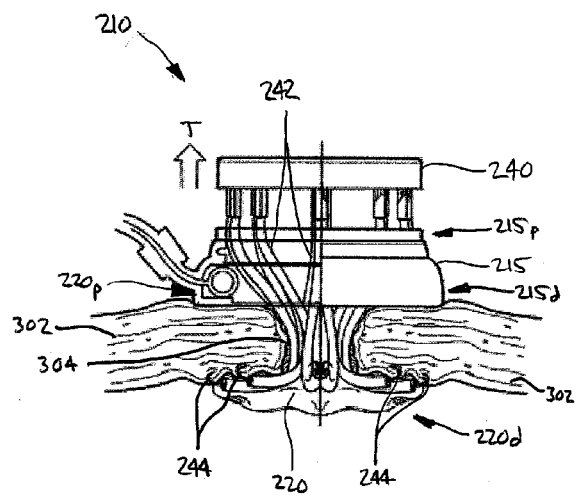
FIG. 5E is a cross-sectional side view of the surgical access device of FIG. 5D showing the retractor being removed from the housing and the wound closure component engaging tissue adjacent to the surgical incision.
Figure 5F:
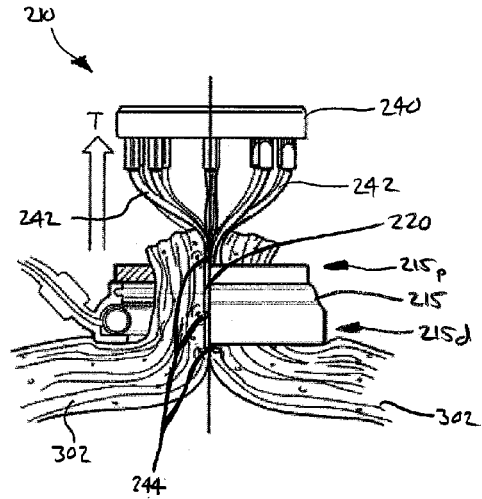
FIG. 5F is a cross-sectional side view of the surgical access device of FIG. 5E showing the proximal end of the retractor removed from the housing and the wound closure component moving tissue from one side of the surgical incision toward tissue from a second side of the surgical incision.

The hooks 244 of the wound closure component 240, which as shown in FIGS. 5D-5F are coupled to the distal end of the suture strands 242, can be configured to engage the tissue 302 adjacent to the distal end of the surgical opening 304 upon insertion thereof. Alternatively, the hooks can be configured to deploy into tissue in response to an operator's input, such as movement of a particular component of the surgical access device. An operator's input can include, but is not limited to, a mechanical, electrical, electromechanical, or some other form of communicated input to cause the hooks to deploy. In the embodiment shown in FIG. 5D, the hooks 244 are configured to deploy into the tissue 302 upon rotation of the wound closure component 240 in a clockwise direction C.

Figure 5G:
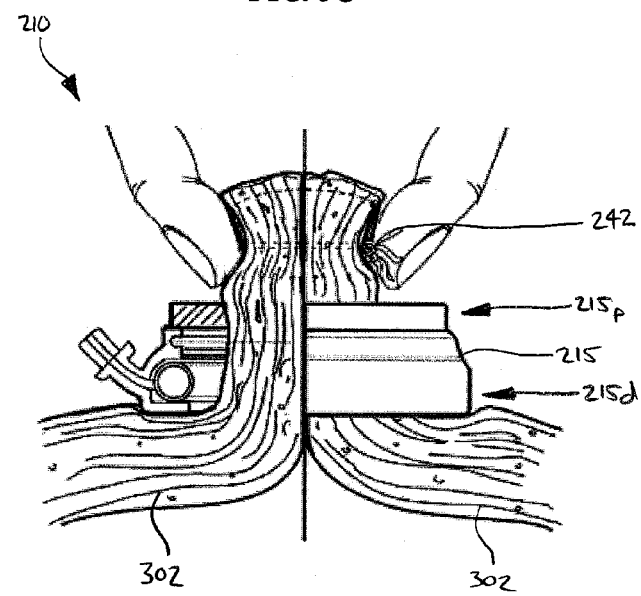
FIG. 5G is a cross-sectional side view of the surgical access device of FIG. 5F showing the tissue pulled toward each other sutured together.

After the wound closure component 240 engages the tissue 302, a variety of techniques can be performed to approximate the tissue adjacent to the surgical opening 304 for wound closure. In the illustrated embodiment, as shown in FIGS. 5E and 5F, the wound closure component 240 can be removed from the wound 304 in a direction T. This, in turn, causes the retractor 220, the suture strands 242, the hooks 244, and the engaged tissue 302 to also move in the direction T, away from the wound 304. The tissue 302 can move from a position below a distal end 215d of the housing 215 to a position above a proximal end 215p of the housing 215, as illustrated in FIGS. 5F and 5G. The wound 304 can then be closed, for example by suturing the wound with the suture strands 242, or alternatively, by another connection means not associated with the surgical access device 210, such as an adhesive or separate suture(s). Optionally, the wound closure component 240 can be disengaged from the suture strands 242 by using any number of techniques, such as, by way of non-limiting example, by pushing a button that triggers the separation or by cutting the suture strands free from the wound closure component.

Although in the illustrated embodiment the wound 304 is closed with tissue 302 extending outside of the body, in other embodiments the wound 304 can be closed within the body, below the housing 215, or after the housing 215 has been removed. Further, while in the illustrated embodiment the wound closure component 240 is configured to couple to the housing 215, in other embodiments it can be configured to pass through the housing 215 and couple to the retractor 220. Still further, any of the housing 215, the retractor 220, and the wound closure component 240 can be integrally formed. A person having skill in the art will recognize that a number of different combinations and configurations can be used in conjunction with a housing, a retractor, one or more seal elements, and one or more wound closure components without departing from the spirit of the invention, including the elimination of one or more components, such as the housing.

Figure 6:
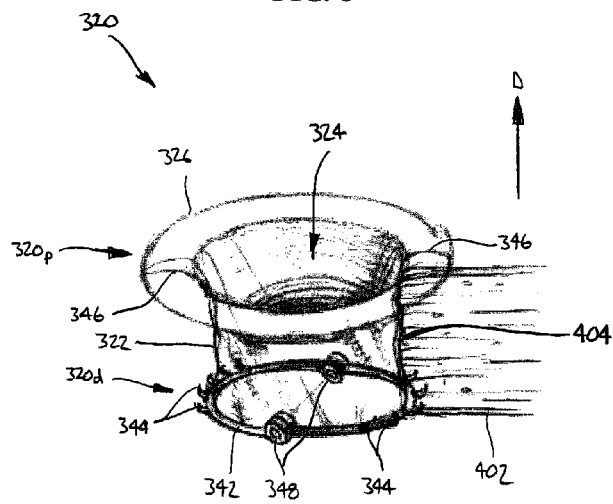
FIG. 6 is a perspective view of another exemplary embodiment of a retractor, the retractor having a wound closure component associated with a distal end thereof.

Another embodiment of a retractor 320 having a wound closure component 340 associated therewith and including a ring 342 at a distal end 320d thereof with a plurality of associated barbs or hooks 344 is illustrated in FIG. 6. The retractor 320 is similar to the retractor 20 of FIG. 1 and can have similar features as those discussed above. Unlike the retractor 20 of FIG. 1, the retractor 320 of FIG. 6 does not include a number of openings for disposing strands of suture in a proximal flange 326 at a proximal end 320p of the retractor 320. It is conceivable, however, that openings can be formed on the proximal flange 326 of the retractor 320 for use with suture strands or the addition of an adhesive, as discussed in greater detail below with respect to FIGS. 11A-11G.

The ring 342 of the wound closure component 340 can be associated with the distal end 320d of the retractor 320 in any number of ways. By way of non-limiting example, the ring can be integrally formed with the distal end of the retractor. Alternatively, the distal end of the retractor can include a sleeve configured to receive the ring, for example in a set or removable configuration. In the illustrated embodiment elongate holding members 346 extend from the proximal flange 326 of the retractor and are coupled to the ring 342 to maintain the ring in a desired location near the distal end 320d of the retractor 320. The holding members 346 can be generally flexible but can be generally rigid enough to maintain a position of the ring 342 as desired.

The ring 342 can be configured in a manner that allows it to close a surgical opening 404. As shown, the ring 342 can include hinges 348 that allow the ring to fold (FIG. 7) for ease of inserting into a lumen 324 of the retractor 320 and to effect a tissue approximation. More particularly, as a force is applied in a direction D, e.g., through holding members 346, the hooks 344 can swing around the hinge 348, toward each other, which in turn causes tissue 402 on either side of an incision to which the hooks are engaged to approximate. While in the illustrated embodiment the hinge 348 is used to approximate the hooks 344 toward each other, other mechanisms can also be used to create a similar effect.

The ring 342 can generally have any size and shape, and can be made from any number of materials, all of which can depend, at least in part, on the size of the retractor and other components with which it will be used, the size of the incision with which it will be used, and the type of surgical procedure with which it will be used. As shown, the ring 342 is substantially circular and includes five hooks 344 on each side of the ring. Any number of hooks 344 can be used. The ring 342 can have a diameter that is approximately equal to the diameter of the lumen 324 extending through the retractor 320. The ring 342 can generally be semi-rigid, and non-limiting examples of materials that can be used to form the ring include stainless steel, such as from the 300 series, nitinol, and plastic, such as filled nylon.

Figure 7:
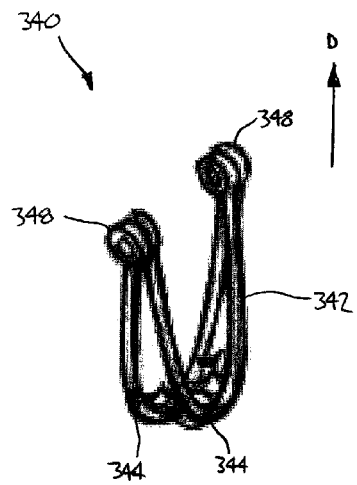
FIG. 7 is a perspective view of the wound closure component of FIG. 6 in a folded configuration.

FIGS. 8A-8G illustrate an embodiment of a surgical access device 410 that includes a wound closure component like that of FIGS. 6 and 7 and a retractor. More particularly, the surgical access device 410 includes a housing 415, a retractor 420, and a wound closure component 440 coupled to the retractor and that includes a ring 442 having barbs or hooks 444 disposed around a circumference thereof. The housing 415 can be configured and used in a manner similar to the housing 215 discussed with respect to the surgical access device 210 of FIGS. 5A-5G. Further, seal elements 418 can be included and associated with at least one of the housing 415, the retractor 420, and as shown, the wound closure component 440, as also discussed with respect to the surgical access device 210 of FIGS. 5A-5G.

Figure 8A:
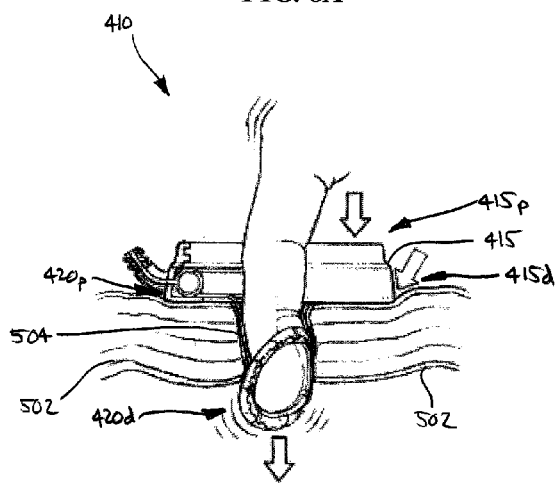
FIG. 8A is a cross-sectional side view of another exemplary embodiment of a surgical access device showing a distal end of a retractor of the device being placed in a surgical incision.
Figure 8B:
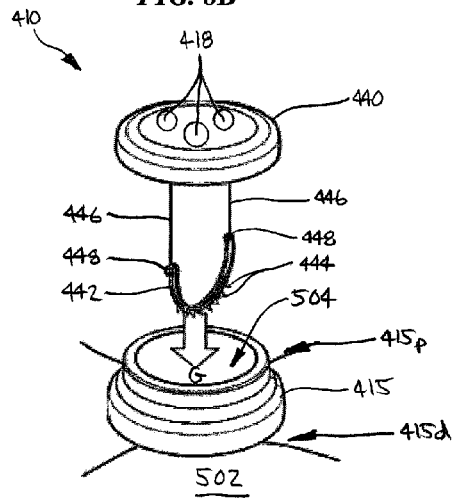
FIG. 8B is a perspective view of the surgical access device of FIG. 8A showing a proximal end of the retractor of the device moving toward a housing of the device and including a wound closure component coupled thereto and in an unengaged position.
Figure 8C:
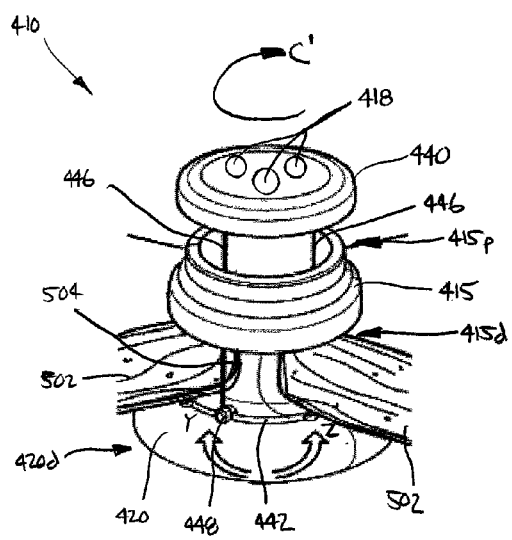
FIG. 8C is a perspective view of the surgical access device of FIG. 8B showing the wound closure component associated with the distal end of the retractor and in an extended engaged position.
Figure 8D:
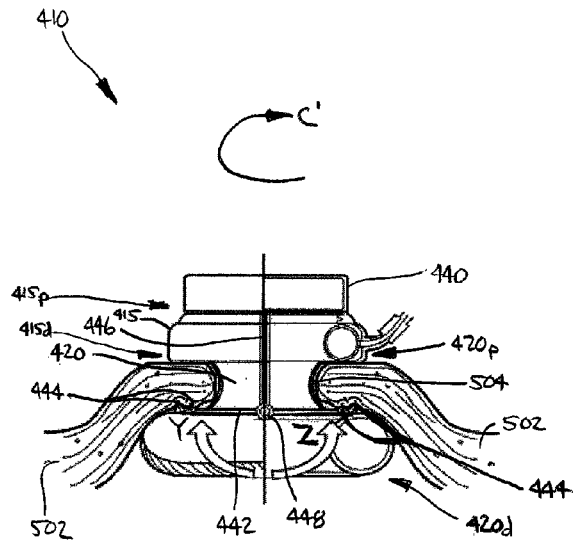
FIG. 8D is a cross-sectional side view of the surgical access device of FIG. 8C also showing the proximal end of the retractor engaged with the housing and the wound closure component in the extended engaged position.

In use, as shown in FIG. 8A, a distal end 420d of the retractor 420 can be disposed in a distal end of the surgical incision 504, thereby retracting tissue away from the surgical incision. As shown, a proximal end 420p of the reactor 420 is located at a proximal end of the surgical incision 504. Subsequently, the wound closure component 440 can be coupled to the proximal end 415p of the housing 415 to form a seal therebetween by moving the wound closure component 440 in a direction G toward the housing 415. The ring 442 of the wound closure component 440, which is coupled to the wound closure component by elongate holding members 446, can pass through the housing 415 and the retractor 420 until it reaches a distal end 420d of the retractor 420. The ring 442 can optionally be coupled to the distal end 420d of the retractor, or it can be held within the general vicinity thereof by the elongate holding members 446. As shown in FIG. 8B, during insertion, the ring 442 can be in an undeployed, folded configuration in which the hooks 444 along a circumference of the ring are proximate to each other and the ring is folded at hinges 448.

Once a desired location for the ring 442 is reached, the wound closure component 440 can be actuated to engage the tissue 502 adjacent to the distal end 420d of the retractor 420. Actuation of the wound closure component 440 can cause the hooks 444 to move away from each other and place the ring 442 in its circular, deployed configuration, illustrated in FIGS. 8C and 8D. As shown, upon deployment, the hooks 444 can engage the tissue 502 to hold and/or retract the tissue. Deployment of the ring 442 can occur in response to any number of inputs, including input from the operator. As shown, rotation of the wound closure component 440 in a clockwise direction C' causes the ring 442 to unfold in directions Y and Z and the hooks 444 to engage the tissue 502 near the distal end of the surgical incision 504.

Figure 8E:
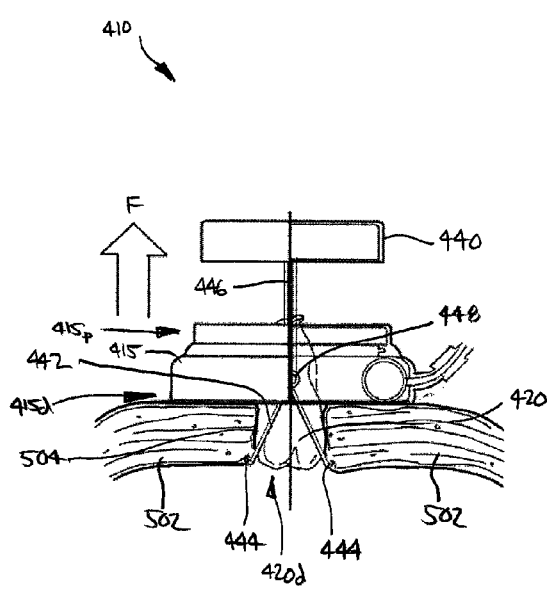
FIG. 8E is a cross-sectional side view of the surgical access device of FIG. 8D showing the retractor being removed from the housing and the wound closure component in a partially retracted engaged position to move tissue from one side of the surgical incision toward tissue from a second side of the surgical incision.
Figure 8F:
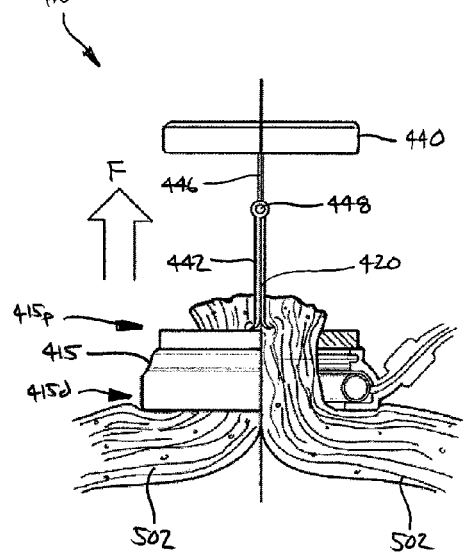
FIG. 8F is a cross-sectional side view of the surgical access device of FIG. 8E showing the retractor removed from the housing and the wound closure component in a fully retracted engaged position such that tissue from the one side of the surgical incision contacts tissue from the second side of the surgical incision.
Figure 8G:
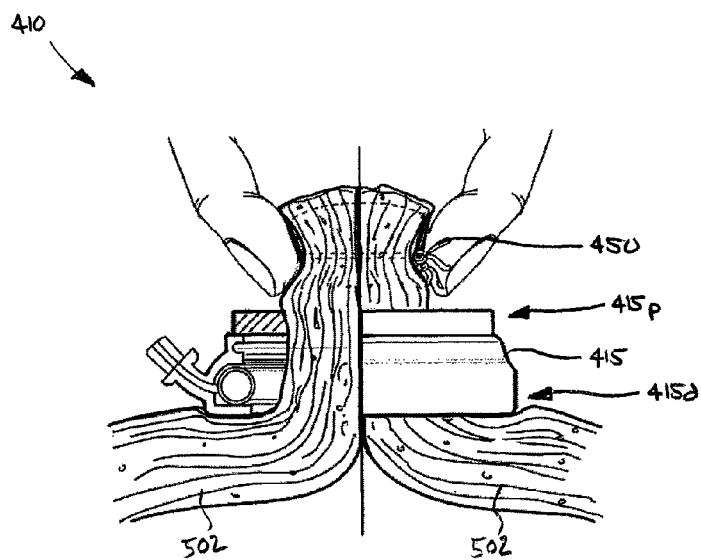
FIG. 8G is a cross-sectional side view of the surgical access device of FIG. 8F showing the tissue sutured together.

As illustrated in FIGS. 8E and 8F, after the wound closure component 440 engages the tissue 502, the wound closure component 440 can be moved in a direction F away from the surgical opening to fold the ring 442 and bring the tissue together. The tissue 502 can be pulled from a position below a distal end 415d of the housing 415 to a position above a proximal end 415p of the housing, as illustrated in FIGS. 8F and 8G. The ring 442 can be removed from the tissue by disengaging the hooks 444 from the tissue in a variety of ways, including, but not limited to, by hand or by an automated command that retracts the hooks inside the ring. The wound 504 can then be closed using a number of techniques, including, as shown in FIG. 8G, by suturing the wound together with a suture 450. Upon completion of the procedure, the retractor 420, the seal elements 418, and the wound closure component 440, as well as the housing 415, can be removed such that no outside component other than the suture 450 used to close the wound 504 remains associated with the tissue 502.

Similar to the surgical access device 210, different configurations of the surgical access device 410 can include different locations for approximating the tissue 502 and closing the wound 504 and different combinations and configurations of components such as the housing 415, the retractor 420, and the wound closure component 440 without departing from the spirit of the invention.

Figure 9A:
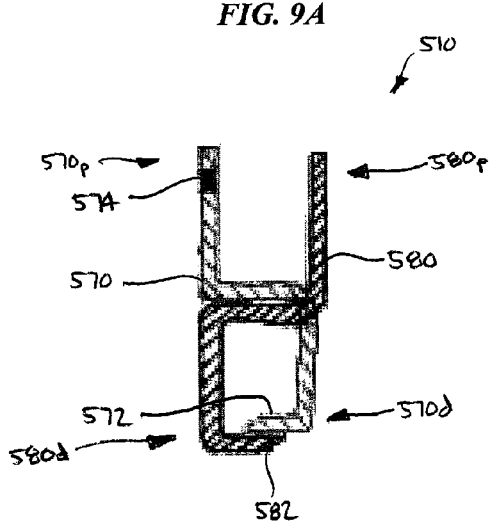
FIG. 9A is a cross-sectional side view of one exemplary embodiment of a wound closure device for closing a surgical incision.
Figure 9B:
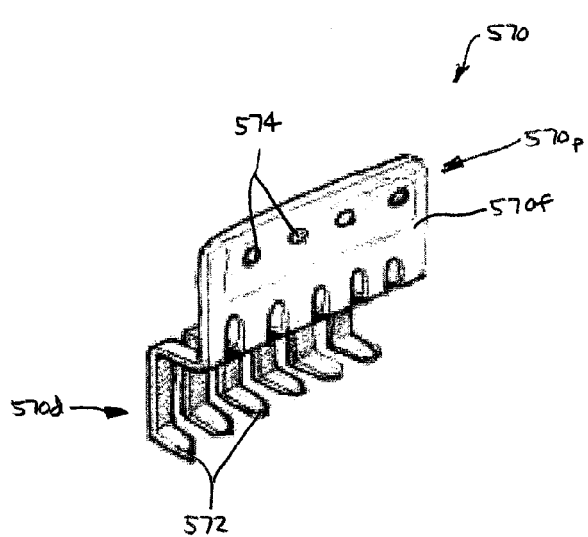
FIG. 9B is a perspective front view of one rake of the wound closure device of FIG. 9A.
Figure 9C:
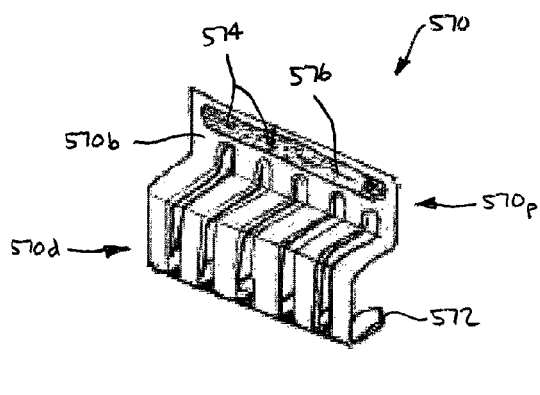
FIG. 9C is a perspective back view of the rake of FIG. 9B.

While the illustrated embodiments discussed thus far include wound closure components associated with retractors, in other embodiments the wound closure components can be separate from the retractors. One embodiment of a wound closure tool 510 is illustrated in FIGS. 9A-9C. The tool 510 can include two tissue-engaging rakes 570, 580, one for engaging each side of a surgical opening. As shown, the rakes 570, 580 can include teeth 572, 582 disposed on a distal end 570d, 580d thereof, respectively, and configured to engage tissue. The rakes 570, 580 can be symmetrically opposed, although they do not have to be. In fact, there can be any number of rakes, any number of teeth on the rakes, the rakes can be made from a variety of materials, and they can have a variety of shapes, sizes, and configurations depending at least in part on the size of the incision and/or components of a surgical access device with which they will be used and the type of surgical procedure with which they will be used. Generally, proximal ends 570p, 580p of the rakes 570, 580 can be long enough to allow for the rakes to be closed from a location outside of the body. Alternatively, a further device, such as handles, can be associated with the proximal ends 570p, 580p of the rakes 570, 580 to operate the tool 510. Movement of the proximal ends 570p, 580p moves the distal ends 570d, 580d, respectively, to desired locations. The distal ends 570d, 580d can engage tissue adjacent to a distal end of a surgical incision, and thus movement of the distal ends by way of the proximal ends 570p, 580p can move the tissue of the surgical incision toward or away from each other as desired.

Figure 10A:
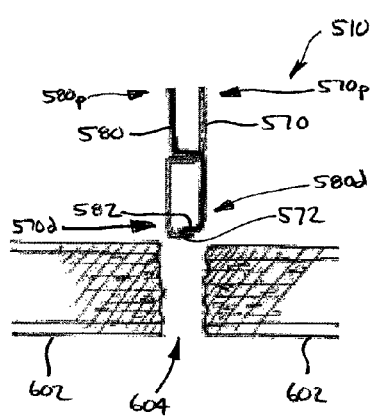
FIG. 10A is a cross-sectional side view of the wound closure device of FIG. 9A showing the device being disposed in a surgical incision.

In one exemplary embodiment each rake 570, 580 is made from two different materials—the proximal ends 570p, 580p include a reinforced flexible polymer and the distal ends 570d, 580d include an absorbable polymer that can remain disposed in the body after the procedure is complete. Optionally, as shown in FIG. 9B, a front side 570f of the proximal end 570p can include one or more openings 574, and, as shown in FIG. 9C, a back side 570b of the proximal end 570p can include an adhesive 576 to assist in securing the wound together, as described below with respect to FIGS. 10A-10C. In one exemplary embodiment the adhesive 576 can adhere to tissue but not to components of a surgical access device, such as a retractor. The openings 574 and adhesive 576 can also be included as part of the rake 580. Further, at least a portion of the rakes 570, 580 can include or be coated with an antibiotic composition.

Figure 10B:
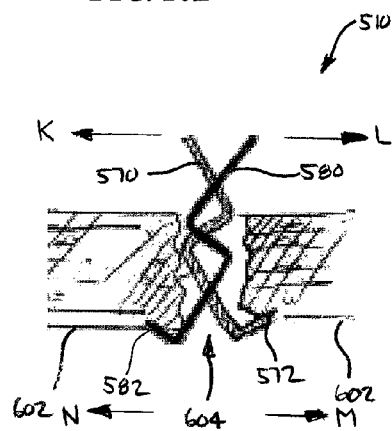
FIG. 10B is a cross-sectional side view of the device of FIG. 10A showing distal ends of the device engaging tissue adjacent to a distal end of the surgical incision.
Figure 10C:
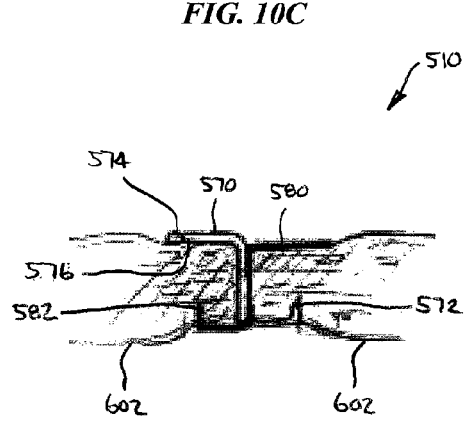
FIG. 10C is a cross-sectional side view of the device of FIG. 10B showing tissue from one side of the surgical incision brought toward tissue from a second side of the surgical incision.

In use, the tool 510 can be inserted into a surgical opening 604 formed in tissue 602. During insertion, the rakes 570, 580 can each be in a generally vertical configuration, illustrated in FIG. 10A, thereby allowing the tool 510 to have a minimum width to facilitate ease of deployment and prevent unnecessary damage to the tissue 602 in which it is being disposed. Once the rakes 570, 580 are positioned in a desired location, the proximal ends 570p, 580p can be moved in directions K and L, as shown in FIG. 10B, which in turn causes the distal ends 570d, 580d to move in directions M and N, respectively. When the distal ends 570d, 580d move in the directions M and N, they can engage the tissue 602. Further movement of the proximal ends 570p, 580p in the directions K and L, and thus further movement of the distal ends 570d, 580d in the directions M and N, can approximate the tissue 602 to allow the surgical incision 604 to be closed. The tissue 602 can be sutured or otherwise mated as discussed with respect to other embodiments. In some embodiments the proximal ends 570p, 580p can continue to move until they are in a generally horizontal configuration, shown in FIG. 10C.

In embodiments in which at least one of the rakes 570, 580 includes openings 574 and/or adhesives 576 as part of the proximal end 570p, and/or in embodiments in which the distal ends 570d, 580d of at least one of the rakes 570, 580 are made of an absorbable material, the rakes 570, 580 can remain associated with the incision 604 even after the procedure is completed. More particularly, sutures or staples can be inserted through the openings 574 on the front side 570f of the proximal end 570p to couple the rake 570 to the tissue. Likewise, the adhesive 576 disposed on the back side 570b of the proximal end 570p can join with the tissue 602 to further secure the rake 570 to the tissue 602. While the illustrated embodiment does not include one or more surgical access device components, such as a retractor, the tool 510 can also be used with such components.

FIGS. 11A-11G illustrate an embodiment of a surgical access device 610 that includes a wound closure component that includes an adhesive and a retractor. More particularly, the surgical access device 610 includes a housing 615, a retractor 620, and a wound closure component 640 associated with a distal end 620d of the retractor 620. The housing 615 can be configured and used in a manner similar to the housing 215 discussed with respect to the surgical access device 210 of FIGS. 5A-5G. Further, seal elements 618 can be included and associated with at least one of the housing 615, the retractor 620, and as shown, the wound closure component 640, as also discussed with respect to the surgical access device 210 of FIGS. 5A-5G. The wound closure component 640 can include a manifold 642 that is configured to allow an adhesive to be applied from a location outside of the body to locations at the distal end 620d of the retractor 620. As shown, the manifold 642 extends from an entry port 648 located on a top surface of the wound closure component 640 to the distal end 620d of the retractor 620. The distal end 620d of the retractor 620 includes a number of openings 628 formed therein. Thus, when a fluid, such as an adhesive, is inserted through the manifold 642, it travels through the wound closure component 640, the housing 615, and the retractor 620 and out the openings 628 of the distal end 620d of the retractor. While in the illustrated embodiment the manifold 642 includes a single tube feeding a number of openings 628, in an alternative embodiment each opening can include its own tube to receive a fluid disposed therethrough. In such embodiments, each tube can meet at a common entry point so a fluid can be inserted into the manifold via a single entry point.

Figure 11A:
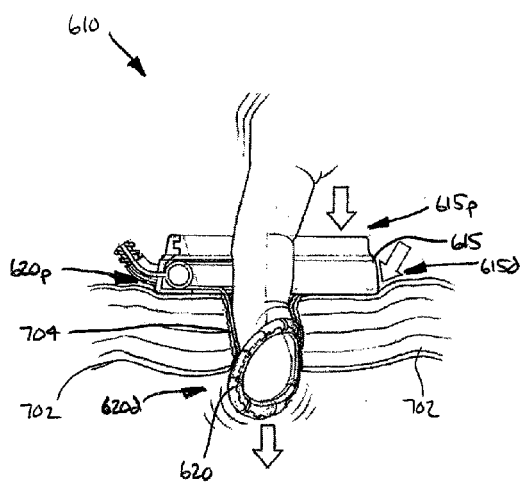
FIG. 11A is a cross-sectional side view of still another exemplary embodiment of a surgical access device showing a distal end of a retractor of the device being placed in a surgical incision.
Figure 11B:
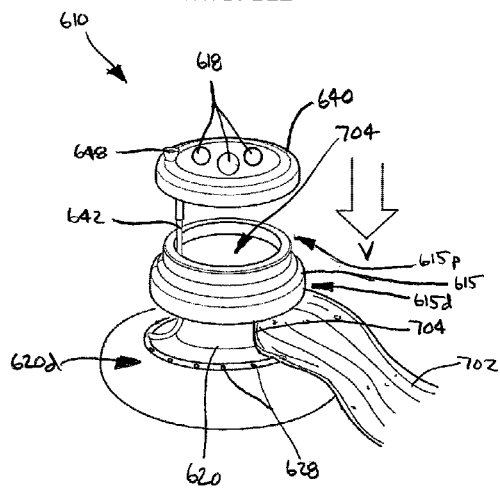
FIG. 11B is a perspective view of the surgical access device of FIG. 11A showing a proximal end of the retractor of the device moving toward a housing of the device and including a wound closure component in communication with the distal end of the retractor.
Figure 11C:
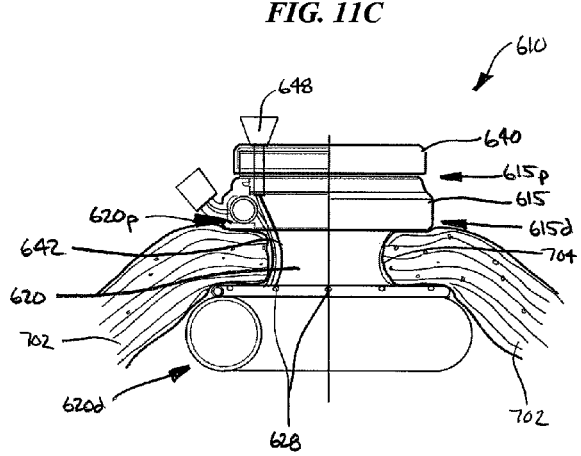
FIG. 11C is a cross-sectional side view of the surgical access device of FIG. 11B showing the proximal end of the retractor engaged with the housing.
Figure 11D:
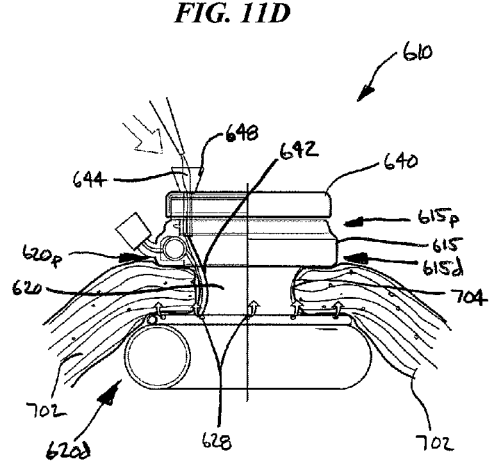
FIG. 11D is a cross-sectional side view of the surgical access device of FIG. 11C showing an adhesive being added to the wound closure component and the adhesive engaging tissue adjacent to the surgical incision by way of holes formed in the distal end of the retractor.
Figure 11E:
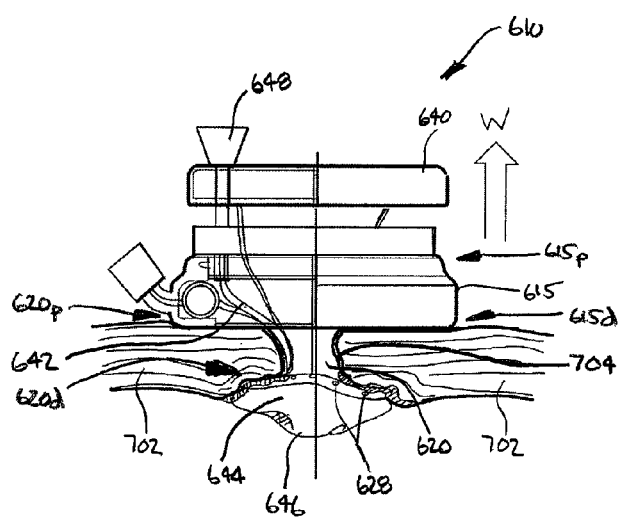
FIG. 11E is a cross-sectional side view of the surgical access device of FIG. 11D showing the retractor being removed from the housing and the adhesive hardening to form a bridge between one side of tissue from the surgical incision and a second side of tissue from the surgical incision.
Figure 11F:
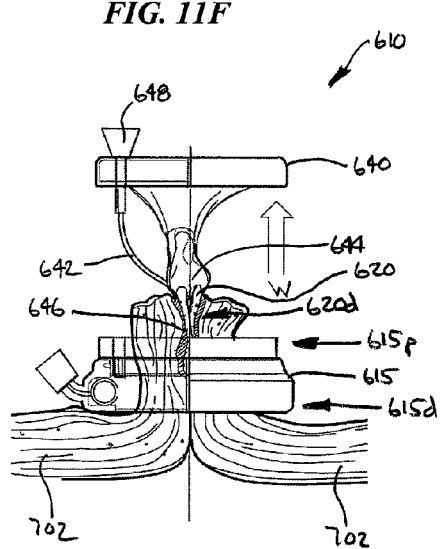
FIG. 11F is a cross-sectional side view of the surgical access device of FIG. 11E showing the retractor removed from the housing and tissue from the one side of the surgical incision contacting tissue from the second side of the surgical incision.
Figure 11G:
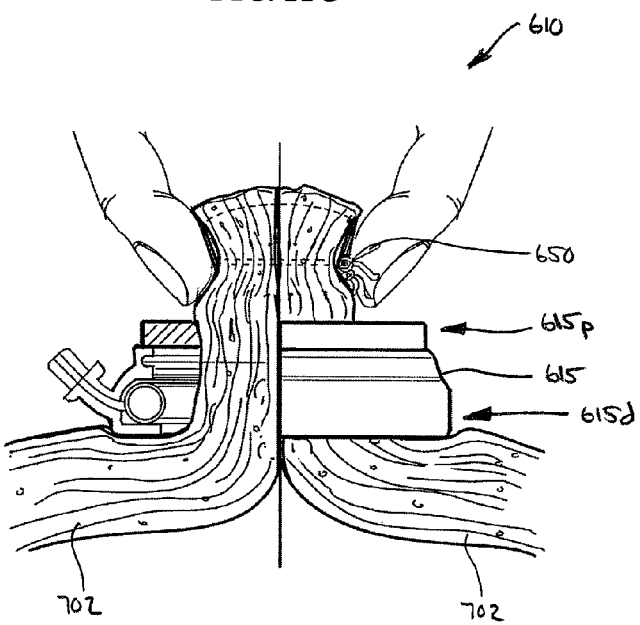
FIG. 11G is a cross-sectional side view of the surgical access device of FIG. 11F showing the tissue sutured together.

In use, as shown in FIG. 11A, the distal end 620d of the retractor 620 can be disposed in a distal end of the surgical incision 704, thereby retracting tissue away from the surgical incision. Subsequently, the wound closure component 640 can be moved toward the housing 615 in a direction V, as shown in FIG. 11B, and coupled to the proximal end 615p of the housing 615 to form a seal therebetween, as shown in FIG. 11C. As shown in FIG. 11D, an adhesive 644 can be added to the manifold 642 at the entry port 648. This, in turn, can cause the adhesive 644 to flow out of the openings 628 in the distal end 620d and form a bridge 646 between tissue 702 from a first side of the surgical incision 704 and tissue 702 from a second side of the surgical incision 704, as illustrated in FIG. 11E. Any adhesive can be used, but it can generally be preferable to include an adhesive that adheres to tissue but not to a retractor so that a retractor can be removed upon completion of the procedure As illustrated in FIGS. 11E and 11F, once the two sides of the opening 704 are adhered together, or while they are being adhered together, the wound closure component 640 can be moved in a direction W away from the opening, which in turn causes the adhesive 644 and the tissue 702 to also move in the direction W. The tissue 702 and the adhesive 644 can thus move from a position distal of a distal end 615d of the housing 615 to a position proximal of a proximal end 615p of the housing 615. The tissue 702 can be mated solely by the adhesive 644 already disposed therein, or alternatively, as shown in FIG. 11G, a suture 650 or other mechanism for securing tissue together can be used to reinforce the bond formed by the adhesive 644.

Similar to the surgical access devices 210, 410, different configurations of the surgical access device 610 can include different locations for approximating the tissue 702 and closing the wound 704 and different combinations and configurations of components such as the housing 615, the retractor 620, and the wound closure component 640 without departing from the spirit of the invention.

A person having skill in the art will recognize that many of the configurations and techniques disclosed herein can be mixed and matched as desired. For example, a wound closure component can include both sutures with hooks disposed on a distal end thereof and a ring having hooks formed along a circumference thereof. Similarly, adhesives can be used in conjunction with components that include hooks, or alternatively, a tool like the tool 510 of FIGS. 9A-9C and 10A-10C can be coupled to or incorporated with a retractor to form a single device. Further, any of the retractors disclosed herein can be used independently as a surgical access device, or alternatively, can be included as one component of a surgical access device. Methods and mechanisms used to mate tissue from one side of a surgical opening to another side of a surgical opening can be many, and thus sutures, staples, and adhesives are only three examples of many that can be used in conjunction with the disclosed embodiments.

A person skilled in the art will appreciate that the present invention has application in conventional endoscopic and open surgical instrumentation as well application in robotic-assisted surgery. For instance, by way of non-limiting example, the tool 510 of FIGS. 9A-9C and 10A-10C can be used in minimally-invasive surgeries, or alternatively, can be used in broader, open surgeries, including those surgeries that incorporate a hand-port.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical access device, comprising:
   a housing having an opening extending therethrough and configured to be positioned adjacent to a surgical incision;
   a flexible retractor removably and replaceably coupled to the housing and configured to be positioned within the surgical incision to provide access to a body cavity, the retractor having a proximal end and a distal end; and
   a wound closure component associated with the distal end of the retractor, the wound closure component having a plurality of hooks and a plurality of strands of suture extending through the retractor from the proximal end to the distal end, each hook of the plurality of hooks being coupled to one strand of suture of the plurality of strands of suture, the wound closure component being configured to engage tissue adjacent to the surgical incision with the plurality of hooks and selectively move tissue from one side of the surgical incision toward a second side of the surgical incision to assist in closing the surgical incision, and the plurality of strands of suture including an actuating suture configured to collapse a distal end of the wound closure component.

2. The surgical access device of claim 1, wherein the distal end of the wound closure component further comprises a distal ring through which the actuating suture is disposed, the actuating suture being configured to collapse the distal ring to close the surgical incision.

3. The surgical access device of claim 1, wherein proximal ends of strands of suture of the plurality of strands of suture are configured to be approximated and pulled together in a direction away from the surgical incision, thereby pulling closer together the tissue with which the plurality of hooks is engaged.

4. The surgical access device of claim 3, further comprising an actuation mechanism coupled to the proximal ends of the strands of suture and configured to approximate the strands of suture toward each other and in a direction away from the surgical incision.

5. A flexible retractor for use in a surgical procedure, comprising:
   a body having a proximal end and a distal end with a lumen extending therethrough and defining a working channel; and
   a wound closure component associated with the distal end, the wound closure component having a plurality of hooks and a plurality of strands of suture extending through the body from the proximal end to the distal end, each hook of the plurality of hooks being coupled to one strand of suture of the plurality of strands of suture, the wound closure component being configured to engage tissue adjacent to a surgical incision with the plurality of hooks and approximate tissue adjacent to the surgical incision to assist in closing the surgical incision, and the plurality of strands of suture including an actuating suture configured to collapse a distal end of the wound closure component.

6. The flexible retractor of claim 5, wherein the distal end of the wound closure component further comprises a distal ring through which the actuating suture is disposed, the actuating suture being configured to collapse the distal ring to close the surgical incision.

7. The flexible retractor of claim 5, wherein the plurality of strands of suture are configured to be manipulated to approximate the tissue with which the plurality of hooks is are engaged.

8. A method for repairing a surgical wound, comprising:
positioning a surgical access retractor through an opening in tissue, the retractor including a wound closure component having a distal ring, a plurality of hooks, and a plurality of strands of suture disposed through and around the distal ring, wherein each hook of the plurality of hooks is coupled to one strand of suture of the plurality of strands of suture and the plurality of strands of suture including an actuating suture;
engaging the plurality of hooks with tissue adjacent to a distal end of the retractor;
manipulating the actuating suture to collapse the distal ring to approximate tissue adjacent to the opening in tissue, thereby closing the surgical wound; and
suturing the approximated tissue.

9. The method for repairing a surgical wound of claim 8, further comprising moving the wound closure component toward an outside environment.

10. The method for repairing a surgical wound of claim 8, further comprising cinching the plurality of strands of suture coupled to the tissue adjacent to the distal end of the retractor toward each other.

11. The method for repairing a surgical wound of claim 8, wherein the step of manipulating the actuating suture to collapse the distal ring further comprises applying tension to the actuating suture.

* * * * *